United States Patent
Herzog

(10) Patent No.: US 9,652,969 B2
(45) Date of Patent: May 16, 2017

(54) PORTABLE DEVICE FOR IMPROVING HYGIENE AND METHOD

(71) Applicant: United-Ventures GmbH, Rodenbach (DE)

(72) Inventor: Andreas Herzog, Frankfurt (DE)

(73) Assignee: United-Ventures GmbH, Rodenbach (DE)

( * ) Notice: Subject to any disclaimer, the term of this patent is extended or adjusted under 35 U.S.C. 154(b) by 0 days.

(21) Appl. No.: 14/784,343

(22) PCT Filed: Apr. 4, 2014

(86) PCT No.: PCT/EP2014/056837
§ 371 (c)(1),
(2) Date: Oct. 14, 2015

(87) PCT Pub. No.: WO2014/170145
PCT Pub. Date: Oct. 23, 2014

(65) Prior Publication Data
US 2016/0093194 A1    Mar. 31, 2016

(30) Foreign Application Priority Data

Apr. 16, 2013    (DE) ........................ 10 2013 006 494

(51) Int. Cl.
G08B 23/00    (2006.01)
G08B 21/24    (2006.01)
G06F 19/00    (2011.01)
G08B 3/10    (2006.01)

(52) U.S. Cl.
CPC ......... *G08B 21/245* (2013.01); *G06F 19/327* (2013.01); *G08B 3/10* (2013.01)

(58) Field of Classification Search
CPC ........ G08B 21/245; G08B 3/10; G06F 19/327
USPC ...................................................... 340/573.1
See application file for complete search history.

(56) References Cited

U.S. PATENT DOCUMENTS

2010/0073162 A1* 3/2010 Johnson ............... G08B 21/245
                                                         340/540
2012/0055986 A1  3/2012 Sahud
2014/0327545 A1* 11/2014 Bolling ................ G08B 21/245
                                                         340/573.1

FOREIGN PATENT DOCUMENTS

| DE | 102011009240 A1 | 7/2012 |
| DE | 102012105368 A1 | 1/2013 |
| JP | 2009223775 A | 10/2009 |
| JP | 2010010982 A | 1/2010 |

(Continued)

OTHER PUBLICATIONS

International Preliminary Report on Patentability and Written Opinion in International Application No. PCT/EP2014/056837 dated Oct. 20, 2015.

(Continued)

*Primary Examiner* — Kerri McNally
(74) *Attorney, Agent, or Firm* — Marshall, Gerstein & Borun LLP

(57) ABSTRACT

A portable device for improving hygiene, comprising at least one warning unit that cooperates with a unit for detection of a disinfection treatment in such a way that a signal can be activated, said warning unit being operatively connected to at least one step counting unit; and, a method and a system for improving hygiene in medical facilities, including the use of a portable device.

16 Claims, 2 Drawing Sheets

(56) References Cited

FOREIGN PATENT DOCUMENTS

WO     WO-02091297 A1    11/2002

OTHER PUBLICATIONS

Figure 1:
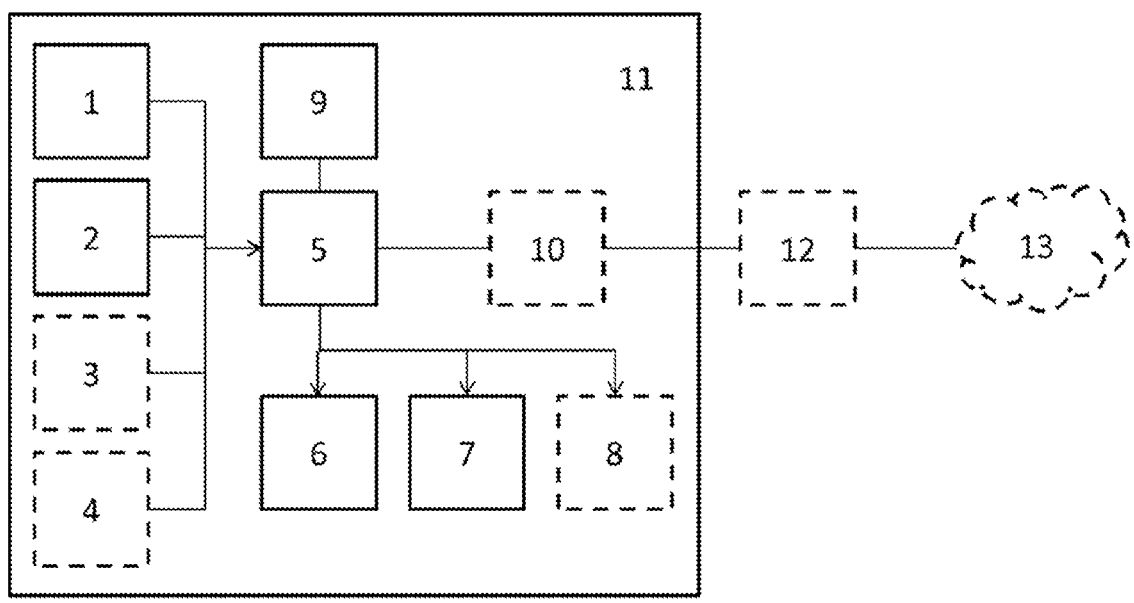

International Search Report from International Application No. PCT/EP2014/056837 dated Jul. 15, 2014.
German Office Action from Application No. 10 2013 006 494.5 dated Nov. 19, 2013.

* cited by examiner

PORTABLE DEVICE FOR IMPROVING HYGIENE AND METHOD

The present invention relates to a portable device for improving hygiene as well as a method.

BACKGROUND

Adequate hand hygiene is important in many industries, such as hospitals and care homes, in order to avoid nosocomial infections, in the food industry and manufacturing to avoid contamination, as well as all areas where the chain of infection for pathogens and contamination with the typical vector "hand" needs to be interrupted. Hand hygiene is especially crucial in medical facilities.

Compliance with hand hygiene rules by staff and visitors of facilities is often not optimal. Reasonable or required hand hygiene actions are not performed, for instance because they are forgotten at the necessary time.

In order to improve compliance, the following basic approaches are used:

Timely reminder of hand hygiene to trigger a hand hygiene action as well as detection of a hand hygiene action that is necessary according to the rules. This measure is related to the target value for hygiene actions.

Quantitative collection of hand hygiene actions or appropriate surrogate parameters in order to obtain insight that leads to further measures (e.g., training) to improve hand hygiene behavior. This approach is related to the actual value of hygiene actions.

Increased transparency of the individual hand hygiene behavior in order to enable self-control, control or reminders by third-parties. This measure is related to the relationship between actual and target value of hygiene actions.

PRIOR ART

Prior art for reminders of hand hygiene (approach 1) as well as the detection of a required hand hygiene action consists primarily of zone-based and time-based methods. With zone-based methods, entry in and exit from predefined zones is monitored with the appropriate technology (e.g., wireless technology, optical capture) and a signal to the staff is issued or a report is generated according to specific algorithms. Time-based methods send reminders of hand hygiene in specific intervals that do not necessarily correspond to the indications for hand hygiene.

A disadvantage of zone-based methods is that specific zones have to be predefined (before the systems or devices for the hand hygiene reminders are applied) and monitored with typically stationary technology (e.g., RFID transmitters). This requires costly local installation work. In addition, flexibility is restricted. In the use case of a hospital, for example, beds are often moved within rooms so that the affected zones have to be set up again each time.

Another disadvantage of zone-based methods concerns privacy, labor law and liability aspects since the position of a person can be traced at any time. Furthermore, wireless methods for zone monitoring can lead to user adoption difficulties, especially if there is a worry about radiation or interference with other important radio systems or electronic devices in the respective organizational surroundings.

Concerning the capture of hand hygiene actions performed (approach 2), prior art consists of capturing the consumed disinfectant as surrogate parameter or alternatively capturing the number of times stationary disinfectant dispensers have been operated. These approaches can only achieve a very inaccurate collection of how often hand hygiene actions are performed. When measuring usage, it is not evident whether the disinfectant was consumed due to successful hand hygiene or, for example, due to theft or excessive use of disinfectant. In addition, measuring how often disinfectant dispensers are operated only provides limited insight in whether a hand hygiene action was actually performed for the required amount of time for the used substance to take effect (in case of disinfectant for example at least 30 seconds according to WHO rules). In particular, capturing disinfections with additional non-stationary disinfectant dispensers that according to studies lead to considerably higher disinfectant usage rates (especially pocket bottles) is hardly feasible since this type of capture requires the dispenser systems to be equipped with appropriate technology. Studies have shown, however, that the ubiquitous availability of hand disinfectants leads to significantly higher usage rates and therefore improved hand hygiene behavior. This ubiquitous availability cannot be achieved with elaborate, technologically upgraded stationary dispensers.

Concerning the increased transparency of the individual hand hygiene behavior (approach 3), where actual and target value of hand hygiene actions are correlated with each other, prior art uses diverse capture systems and devices at different locations to detect hand hygiene actions as well as the necessity of hand hygiene actions. In prior art this information is collected in a central location (typically via wireless connections), evaluated and submitted to a signaler (normally on the body of the person that needs to perform a disinfection). The wireless communication can be unfavorable in specific organizational environments due to non-excludable electromagnetic interference with sensitive devices or due to subjective opinions of users. With its several involved components, the system is altogether complex and therefore sophisticated and delicate.

Patent DE 10 2011 009 240 A1 describes a system for hygiene control. Essentially, it is based on a proximity sensor and reminds the user via an acoustic signal of using the disinfectant. It is also suggested that the warning sound is issued after a defined time span after an individual approaches or leaves the vicinity of the sensor. RFID tracking is proposed to mark the entering individual. One of the disadvantages of this solution is that the dimensions of all hygiene areas have to be completely predefined, thereby restricting the operative flexibility, for example, of hospital operations, that proximity sensors have to be installed and that the system as a disinfectant dispenser does not allow for the usage of mobile pocket bottles and additional dispensers, which improve hygiene.

Patent DE 10 2012 105 368 A1 also describes a system for hygiene control. It proposes a sensor at cleaning stations/sinks or the like in combination with a portable identification means in order to monitor compliance with hygiene regulations. Monitoring is performed via a capacitive sensor that responds when the user wets his/her hands with water/disinfectant. Sender and receiver communicate wirelessly. It is proposed to send a warning sound either when the user has not visited a cleaning station for a certain amount of time or when he/she has entered or left a certain area. This solution is combined with room surveillance, which makes it problematic with regards to privacy laws and user adoption. Furthermore, it requires a great number of sensors to monitor the rooms.

Patent US 2010/0073162 A1 describes a device to send reminders of hand hygiene. In order to detect hand hygiene actions, a combination of motion sensor, gas sensor and if needed acoustic sensor is proposed. The motion sensor is not used for counting steps but only to determine whether objects have been touched. However, since numerous objects are touched very quickly during common workplace activities, without hand hygiene becoming necessary every time, this type of motion tracking leads to significant misinformation on whether a hand hygiene action was necessary. In addition, this invention requires a device being carried on the wrist or near a user's hand in order to be able to detect contact. According to applicable hygiene regulations in many institutions (e.g., hospitals), this is prohibited for reasons of hygiene. Finally, the invention is based on using several sensors and signalers at different locations, which requires data transmission between each of the enclosures and restricts practicality.

Patent JP 20010-010982 A describes a method for distributing the workload of nursing staff. It uses a step sensor for determining the number of steps taken. According to prior art, pedometers are used for measuring the number of steps taken or even the length of a distance covered. The measurement of the number of steps taken seems likely considering the usual use of pedometers.

The present invention on the other hand does not concern measuring the number of steps taken or workload distribution like the cited patent but the determination of a specific event identified by a change of location. This is a wholly different, new and—considering the usual use of a pedometer—surprising purpose.

Patent US 2012/0055986 A1 describes a system for improving hygiene in medical facilities, wherein the system contains a portable data reading unit that can be detected by a door triggering unit if a person equipped with the data reading unit enters a room, as well as a dispenser triggering unit, which can detect a hygiene treatment performed by a person equipped with the data reading unit. A for this document insignificant paragraph explains that the portable data reading unit allows for an evaluation of the wearer's hygiene behavior, presenting an analogy for a pedometer. The exclusive subject of the analogy is the users' desired change of behavior. The mention of the pedometer is in no way connected to the inventive use of a pedometer for detecting a change of location relevant to hygiene. The actual use of a pedometer is in fact explicitly not subject of that pending patent but only mentioned as a metaphor. On the contrary, this mention of a pedometer in connection with another patent for improving hand hygiene without this pedometer being part of the design or connected to the invention shows vividly that there is no relation to the use of a pedometer for detecting a change of location.

Patent US 2010/0073162 A1 mentions a motion sensor, which is not designed as a step sensor, though, but only as a device for capturing a hand movement as it occurs during disinfection. The patent merely describes a specific method for detecting disinfections but not the method for capturing indications for disinfections covered herein.

SUBJECT MATTER OF THE INVENTION

Given prior art, the purpose of the present invention is to provide a technically enhanced hygiene improvement system, specifically in medical facilities, that does not show the disadvantages of traditional methods.

In particular, staff needs to be reminded of hand hygiene actions in time as proscribed by the hand hygiene rules of the WHO—including before and after contact with patients and after leaving the patient environment. With regard to privacy laws and user adoption it should be possible to avoid collecting personalized data during this process. Furthermore, the design of the system should be as easy and cost-effective as possible.

These as well as other not explicitly mentioned tasks, that can easily be derived or deduced from the aspects covered above, are solved with a portable hygiene improvement device according to the invention.

Correspondingly, the present invention provides a portable device for improving hygiene, comprising at least one warning unit that cooperates with a unit for detection of a disinfection treatment in such a way that a signal can be activated, said warning unit being operatively connected to at least one step counting unit.

The invention bypasses the disadvantages—especially with regards to approach 1 detailed above—of the reminder feature by using a basically location-independent approach that still captures the indications for hand hygiene based on the user's change of location.

In a specific embodiment, the invention especially implements the hand hygiene rules that are typically present in an organization. Used around the world and providing the basis for numerous national and organizational hand hygiene regulations, the hand hygiene rules of the WHO prescribe a hand hygiene action before contact with patients, after contact with patients as well as after contact with a patient environment, among others. In other words, in these cases there is an indication for hand hygiene.

The present invention is based on the insight that these indications are related to a user's change of location. Surprisingly, the goals of hygiene improvement explained above particularly in medical facilities can be achieved by connecting changes of location due to specific step movements to a reminder of a hygiene action. A change of location normally involves a certain minimum number of steps. By capturing this number of steps these indications can normally be captured as well. Conversely, a change of location marked by a certain minimum number of steps especially for example in a hospital is normally connected to an indication for hand hygiene. This includes, for example, going to the toilet, going from break rooms to patient rooms, etc. Capturing when a certain minimum number of steps has been exceeded is therefore an adequate indicator for when hand hygiene is required.

Thanks to the present invention, users that have to perform a hand hygiene action can also be reminded of this after contact with a patient and after leaving a patient environment without personalized data being collected by means of room surveillance. Sophisticated mounted monitoring systems and communication between mounted and mobile units of a monitoring system become unnecessary.

The invention also allows for a specific embodiment that combines the step count with other indicators for a requirement for hand hygiene, e.g., receiving an infrared signal in specific especially monitored zones, capturing certain movement patterns, distances of time, etc.

With regards to approach 2 (capturing hygiene actions) the invention allows a significantly more accurate capture of actual hand hygiene actions by detecting the presence of disinfectant in high concentration in close proximity to someone's hand—that is highly likely to be due to a hand hygiene action—and additionally monitoring compliance with the mandatory time of exposure to the disinfectant with multiple measurements of the gas concentration. Contrary to prior art in measuring, the invention does not restrict the crucial use of decentralized disinfectant dispensers, which should be available everywhere, due to increased dispenser costs since, according to the invention, hand hygiene events are captured with a mobile device on the wearer's body. In comparison, simply measuring consumption of disinfectant does not provide any insight in actual usage since this could also include theft of excessive usage to manipulate consumption statistics.

In a specific embodiment of the invention, especially when used in hospitals, the used gas sensors are alcohol sensors as since the disinfectants used in hospitals typically contain a significant alcohol concentration.

The inventive portable hygiene improvement device includes at least one warning unit that works in combination with a detection unit for disinfections so that a signal can be triggered. In this context, a warning unit defines a unit that can control a signal on the basis of a detected disinfection treatment. In general, known data processing units or control devices, like microcontrollers, can be used for this purpose. The control device generally intended for the warning unit evaluates the corresponding signal data from the detection unit for disinfection treatments as well as the data from the step counter with suitable algorithms. Depending on the evaluation, the warning unit can activate signals. These signals can be transmitted to the user with visual signals (for example, on an LCD touchscreen or an LED), acoustic signals (for example, over a speaker) or movements (preferably vibrations).

For example, the warning unit can include a control display for showing the disinfection state (e.g., one or more LEDs), a speaker or a unit for generating a vibrating alarm to remind users of a disinfection.

Detection of a hand hygiene operation can be displayed with an appropriate signal, like a green LED lighting up. In a specific embodiment, this signal can only be perceived by the wearer of the inventive device, or in another embodiment for facilitating social control also by people close-by.

When the warning unit determines an indication for hand hygiene after evaluating the signals from the detection unit for disinfection treatments, for example, a light signal can be emitted at the LED (e.g., a red light when using an RGB LED) or an existing light signal that indicates a successful hand hygiene action can be turned off.

In addition, the LED can be used for indicating other relevant operating states of the inventive device, for example, rest period setting or charging state.

To remind users of a necessary hand hygiene action, an alarm can be used. In specific embodiments this can be a vibrating alarm or an acoustic signal. This requires striking a balance between the signal receiving the necessary attention and the wearer accepting the inventive device.

In another specific embodiment of the invention, additional I/O elements for data entry and output (e.g., displays and touchscreens), additional information on situationally indicated hygiene actions, additional measures, background information, etc. can be displayed and interactions with the device wearer can be performed.

Detection units for disinfection treatments are detailed in the prior art section above. For example, wireless connections or RFID chips can be used that send a signal to the warning unit when a user approaches a sensor in order to detect disinfection treatments.

The wireless connections can be implemented by means of, for example, WiFi and/or Bluetooth. Alternatively, an infrared connection is possible as well.

Furthermore, the unit for detecting a disinfection treatment can be equipped with a sensor—for example, a proximity sensor or a capacitive sensor, as described in detail in DE 10 2012 105 368 A1—which determines a disinfection treatment when a disinfectant dispenser is operated. The unit for detecting a disinfection treatment can also be equipped with a switch that enables manual confirmation of a disinfection treatment.

Preferably, the detection unit for disinfection treatments includes at least one gas sensor that preferably detects alcohol, more preferably ethanol and/or propanol. With this design, the detection can occur everywhere and dependent on individual dispensers. Specifically, the duration of a disinfection treatment can be measured simultaneously so that a high standard of hygiene can be achieved.

Using appropriate evaluation software, the gas sensor can detect the presence of chemical substances used for hand hygiene. The chemical substance can either be a necessary component of the disinfectant or a substance that was added for the purpose of detection. Additionally, in a specific embodiment, by repeatedly measuring the presence of the substance over time, a successful hand hygiene action, which is also characterized by a specific time of exposure to the substance, can be determined. Furthermore, this measure can reduce the likelihood of the substance being captured arbitrarily due to usage near the device for other purposes than hand hygiene.

In a specific embodiment of the invention, an alcohol sensor is used as the gas sensor. Since the efficiency of conventionally permitted disinfectants in hospitals are based on alcohol and merely washing your hands with soap does not comply with hand hygiene rules, a performed disinfection can be determined by this. By setting an appropriate threshold for detection (not too high so that every disinfection is detected, but not too low so that other people's disinfections are not detected) and repeating the measurement several times over time (in order to exclude erroneous measurements of an alcohol cloud in the surroundings, for example, from other people's disinfections, and to determine the required time of exposure to the disinfectant), we can achieve high accuracy in capturing disinfection events.

The data captured with the detection unit for disinfection treatments can be evaluated with a separate data processing unit or control device. Furthermore, the warning unit described above can perform this evaluation in a special embodiment.

The warning unit is operatively connected to at least one step counter. In general, the step counter is comprised of an acceleration sensor—preferably a motion sensor with data that enables the identification of a movement pattern using appropriate software. The movement pattern may, for example, correspond to a specified number of successive steps and/or a number of steps with a relatively uniform time between them. With appropriate thresholds for a minimum number of steps and, in a specific embodiment of the invention, also on the basis of an algorithm in combination with other information, this can determine the indications for a disinfection before contact with a patient, after contact with a patient and after leaving a patient environment according to WHO rules with high reliability.

The opportunities for operationalization of step detection are well known in the prior art and described in Ms. Najme Zehra Naqvi et al./International Journal on Computer Science and Engineering (IJCSE), Vol. 4 No. 5 May 2012, ISSN: 0975-3397, or in United States Patent Application 20140074431, or Neil Zhao, Full-Featured Pedometer Design Realized with 3-Axis Digital Accelerometer, Analog Dialogue 44-06, June (2010), among others.

The methods as described above in detail can each be enhanced by detecting a step sequence due to a timely sequence of acceleration values, which can be classified as directly successive steps and/or relatively uniformly timed successive steps. This means that, for example, within a prescribed time interval within which a subsequent step normally follows within an existing step sequence, if no subsequent step is detected, the end of the step sequence is detected. Provided this step sequence exceeds a minimum number of steps, a change of location relevant to hygiene is detected.

In order to identify a movement pattern that corresponds to a prescribed number of successive steps and/or a number of relatively uniformly timed successive steps, time data is processed in addition to acceleration data. Here this time data along with the acceleration data can be carried over into a time interval, within which a subsequent step has to occur in order to be identified as belonging to the step sequence.

The time interval, within which a subsequent step has to occur in order to be identified as belonging to the step sequence, as well as the other time and acceleration thresholds necessary for detection can be predefined by the software for all device wearers in an institution with stricter hygiene requirements (for example, also according to the characteristics of the organization within which the system is used). However, in an advantageous embodiment these values can also be restricted individually according to the characteristics of each wearer's walk, assuming that people have different walking speeds and step and acceleration characteristics. This way, a higher detection accuracy can be achieved. The appropriate parameters for this can be identified during a learning phase. The data collected here can be programmed individually in a device for improving hygiene to be used by a wearer. Furthermore, different classes of devices for improving hygiene can be provided for different wearer groups so that especially tall wearers wear one type while smaller users wear a different type. According to a specific design, a device for improving hygiene can be programmed according to a user at that user's start of work, preferably by entering a code. This input (personalization) can take place at a base station where the device can be charged as described in more detail below. The code can also be submitted wirelessly and/or via an infrared interface to the specific device.

In particular with personalized devices or devices personalizable by code input, the learning phase can also take up a longer period of time. This enables correspondingly tighter limits and thresholds as well as differentiation between different ways of walking (e.g., slow walking, fast walking and running) that occur within that period.

The possible differentiation between different ways of walking (e.g., slow walking, fast walking and running, either determined individually or provided by default) due to acceleration values and time distance between the steps can also be connected to an estimate of each step length. This especially applies when using personalized portable devices, in which the wearer's step length for different ways of walking can be entered, for example, by pressing keys or using a data connection to the portable device. In another embodiment of the invention, individual step lengths can also be determined statistically. For this two absolute positions are determined using an alternative method (e.g., infrared, RFID, Bluetooth, GPS), and the known distance between the two absolute positions is divided by the number of the steps taken.

According to a specific embodiment of the present invention, the distance covered within the step sequence can also be calculated using the step lengths within the uninterrupted step sequence. In this case, the detection of a change of location by the invention using a specific minimum number of steps within an uninterrupted step sequence can be replaced by the detection of a change of location using the estimated distance on the basis of the number of steps within an uninterrupted step sequence.

In another specific embodiment, the acceleration sensor can also capture the wearer's activity and thereby enable you to relate the number of hand hygiene actions and indications for hand hygiene actions to the number of actual staff working hours, which in turn can be significant, for example, for a statistical evaluation. Furthermore, the sensor can detect other movement patterns relevant for indication.

The data captured with the step counter can be evaluated with a separate data processing unit or control device. You can also choose to perform this evaluation with the warning unit described above.

In another embodiment, the warning unit can be connected to one or more step counters in such a way that the data captured with the step counter are transferable to the warning unit and the transferred data in the warning unit can be processed to activate a signal.

Moreover, the device can also include one or more time recording units, which would preferably be operatively connected to the warning unit. This enables supplementary additional reminders to be sent to the device wearer, for example.

The inventive device can furthermore include an IR sensor (infrared sensor) that is operatively connected to the warning unit. This makes it possible to send an additional reminder to the device wearer in certain zones. It also allows for monitoring the step sequence differently, for example, with a decreased threshold for the minimum number of steps after which the warning unit is activated. Furthermore, it creates the possibility for interaction with the user via an infrared remote control (e.g., for entering a personal code).

In a specific embodiment of the invention, the acceleration and gas sensors are supplemented with an additional infrared sensor. In exceptional situations, where relevant changes in location are so small to not be detectable by the acceleration sensor when used as a step sensor, an additional infrared sensor can increase the accuracy of capture. For this purpose, it is possible to mount an infrared sensor above the zone to be captured, that exactly covers the zone to be monitored. The infrared receiver that can be installed in the device receives the individual signal from the infrared sensor and can either directly activate an indication for hand hygiene or, for example, change the threshold for the minimum number of steps. For example, if beds are located very close together in specific situations, thus making step detection alone insufficient for detecting an indication for hand hygiene, incorporating an infrared signal in the algorithm for the decision concerning a hand hygiene action can lead to higher accuracy.

Wireless techniques cannot offer a comparable selectivity when dividing zones. Furthermore, wireless techniques can lead to problems with other devices.

In an especially preferred design, a portable device for improving hygiene can contain one or more units for detecting a disinfection treatment, a capturing unit that detects a change of location based on an uninterrupted step sequence with a specific minimum number of steps, which typically necessitates a hand hygiene action, and a warning unit that is operatively connected to the detection unit and the capturing unit and produces results, which are evaluated and serve as a basis for a signal to the user to perform a hand hygiene action. The capturing unit essentially corresponds to the step counting unit detailed above.

In addition a portable device for improving hygiene can preferably contain one or more units for detecting a disinfection treatment, which can detect a disinfection treatment using a gas sensor and/or by the device user operating a designated key on the portable device and/or by approximation to a disinfectant dispenser wherein the operation of the disinfectant dispenser can be signalled to the portable device using wireless technology, for example.

In another specific embodiment of the invention the portable device includes further sensors or additional input elements. This can enable the device wearer, for example, to inform the device additionally about special working situations, such as activities in the intensive care unit (ICU), performing an aseptic task or contact with bodily fluids. Such an embodiment can enable complete capture of all indications for hand hygiene according to the WHO. In another specific embodiment of the invention, sensors can be used to determine that the user is on a break or in a different situation where hygiene rules do not have to be followed. This can also be specified by a device wearer via input elements.

The device can be equipped with one or more data stores that can store, for example, time data, data on the number of hand hygiene treatments and/or data on the hand hygiene indications according to the number of steps or other detection systems, etc. Preferably, the data store would be operatively connected to the warning unit and/or the detection unit for disinfection treatments. Preferably, all relevant activities, especially all performed hand hygiene actions and all detected indications for hand hygiene, can be stored in a data store together with an exact time stamp.

In a further useful embodiment of the device, the data in the data store can then be transferred to an external computer system by means of a data transfer unit.

It would be advantageous to equip the portable device with one or more data transfer units that are operatively connected to the data store for the data contained in the data store to be transferable to an external computer system.

From this, other statistical or individual information can be derived that increases the transparency of the achieved hygiene standard and helps with identification of further opportunities for improvement with regard to hygiene measures.

An appropriate data transfer unit, which specifically includes an interface for known transfer technologies (e.g., Bluetooth, WiFi or wired standards, such as USB) can transfer the data from the data store to a computer system in order to enable centralised collection of data and statistical evaluation as well as individual access to the data collected.

Here, it should be taken care that potential other wireless systems in the organization are not disrupted by using wireless technology.

The preferably applicable computer system serves for collecting the storage data from the individual inventive devices in an organizational unit. In a preferred embodiment of the invention, the computer system can also be used for charging the battery which could be preferably used for power supply to the inventive devices. For this, the devices are connected to the computer system when the device wearer is finished with his/her relevant activity in order to charge the battery and transfer the stored data.

An inventive special feature of the computer system lies in a potential pooling of the individual portable devices that are used in an organizational unit. This achieves anonymization without having to forego evaluations specific to individual wearers. While it is not possible tracking which individual displays which specific disinfection behavior, it is possible determining, however, that on a certain day one of the device wearers displayed a certain, e.g. objectionable, disinfection behavior. The present invention enables weighing up the effect of anonymization measures, that can drive adoption and if necessary comply with privacy laws, against the advanced control possibilities with a personalization of the inventive devices.

Furthermore, the individual users can be provided with the capability for an individual, access-protected statistical evaluation, even if the use of the portable device is basically anonymous by using a common pool of portable devices, from which devices can be picked that cannot be identified individually and to which these can be returned after use (e.g., at the end of a shift). This is possible if the user provides a personal code only known to him or her to the portable device and/or the system via a suitable interface.

This code can be provided wirelessly or by means of a potential infrared receiver within the portable device. Additionally, checksums can be used to verify that no abuse of others' codes takes place. The record from the removal of the mobile device from the pool to its return to the pool is then allocated to the user that identified himself or herself with the personal code. This enables the creation of individual usage statistics and disinfection behavior statistics that are only accessible to the user, for example, by entering his or her personal secret code or another password in a data processing system. Thus the advantages of anonymity with regard to privacy and user adoption can be combined with the advantages of individual visibility of the user's own data.

The computer system can be used individually or as part of a network. Particularly in larger units, a network (ie. a group of several connected computer systems) can be advisable, for example, in order to allow for statistical control of the individual organizational units. A network comprising of one or more computers can be utilized for transferring, collecting and aggregating the data from the different computer systems that could be set up in different units of a larger organization. In general, a network includes one or more servers that are connected to the respective computer systems via a data connection.

In addition, the data from the network can be made available to different users, such as the organization's administration or the individual wearers of the inventive devices. According to the invention, the data can undergo statistical processing, especially in time series, and be made available in order to initiate improvement measures based on this.

In one possible embodiment of the system, statistical information about the disinfection behavior in different organizational units can be displayed on different end devices, for example, PCs, tablets, mobile devices and others with appropriate user management and access control. The information displayed could be, for example, the number of disinfections per calendar time unit or the number of disinfections for each hour that the portable device was worn or the number of disinfections for each disinfection reminder by the warning unit. Aside from time series analyses, it is also possible to perform comparisons of the respective values for different organizational units.

In a specific embodiment of the invention, the mobile use of the device is facilitated by producing an especially lightweight device. According to prior art, the device weight is currently primarily driven by the power supply, for example, in the form of a battery. Power consumption, especially of the gas sensor, and particularly in the design as an alcohol sensor, is high since the measuring technique in commercially available sensors involves the use of heater current. In one embodiment, the inventive method is intended to reduce power consumption of the gas sensor by regulating the voltage supply to a level under the prescribed voltage according to sensor specifications, contrary to the use of the gas sensor according to the specifications and prior art. Although this reduces the measuring accuracy, the voltage supply is only reduced just enough that the necessary accuracy and speed for the detection of the highly concentrated gas cloud when performing a hand hygiene action is still a given.

In addition, the detection unit for disinfection treatments can include a semiconductor, where the heating voltage for the sensor element is only created for a short amount of time and the signal from the gas sensor element is already measured no more than 250 ms after heating starts.

In another specific embodiment of the invention, the power consumption of the gas sensor is reduced by, contrary to the sensor specifications, not preheating and regulating but measuring the output signal from the sensor very shortly after turning on the heating voltage (no more than 250 ms after activation). During a hand hygiene action with the corresponding high gas concentration, this output signal is sufficiently different from the ordinary output signal, enabling a positive measurement and differentiation. These short term measurements only have to be repeated in intervals (e.g., every second), achieving energy savings for a majority of the time that would otherwise be continuously heated.

A further specific embodiment of the invention leverages a combination of the two energy saving measures mentioned above (namely, reduction of supply voltage and short-term measurements in intervals) in such a way that optimal energy savings are achieved. Here the reduction of the heating voltage leads to a longer necessary time span after which a distinctly discriminating measurement of the critical gas concentration in the short-term interval measurement is possible. But in total a reduction of the supply voltage in combination with the reduction in power consumption by short-term interval measurements leads to lower power consumption than only using one of these energy saving approaches.

Particularly preferred gas sensors are primarily based on semiconductors, such as stannic oxide ($SnO_2$). These sensors are commercially available under the name MQ303A. In the special use case for alcohol sensor MQ303A with a supply voltage of 0.7V (instead of 0.9V according to specifications) after less than 250 ms warm-up time (instead of several minutes or even hours), it is possible to reach a positive decision whether or not an alcohol concentration above the threshold is present. By foregoing the accuracy that is unnecessary for the inventive use, power consumption and thereby the battery weight (the alcohol sensor is by far the greatest consumer when using typical components) are reduced to a fraction of the power consumption that exists when using the alcohol sensor according to specifications and prior art.

Furthermore, it can be provided that the heating voltage is additionally reduced in comparison with the specification value. In this context, the specification value refers to the details from the gas sensor manufacturer.

In a specific embodiment, the method can be refined by choosing the duration of the heating voltage interruption subject to the step frequency measured by the step counter. Note that with a low step frequency the duration of the voltage interruption is greater than with a high step frequency.

The low power consumption in this advantageous embodiment of the invention makes it possible to permanently and automatically measure the presence of a hand hygiene action with the device during a long time span without recharging the energy store, thereby making an explicit activation of the measurement by the user unnecessary. This improves the adoption of the device use considerably.

In a specific embodiment, the invention achieves special advantages concerning basic approach 3 described above—increasing the transparency of the individual hand hygiene behavior—by being able to integrate the detection of necessary hand hygiene actions, the successful completion of hand hygiene actions as well as the signal to the user into a single mobile device thereby eliminating the demand for wireless transmissions and complexity with multiple devices.

A special advantage of the invention is being able to produce it in a very light-weight design, which makes it easy and comfortable to attach to the wearer's work clothes as a mobile device without interfering with freedom of movement. In particular, this makes it possible to attach the device at stomach or chest level, achieving high reliability in detecting hand hygiene actions by measuring the gas concentration.

A further subject matter of the present invention is a system for improving hygiene in medical facilities, which includes one or more dispensers designed for releasing a disinfectant to a user, and one or more portable devices according to the invention covered herein.

Disinfectant dispensers are well known in the professional world. In this scenario, the dispenser can be equipped with a system that can exchange data with the inventive portable device in order to detect a disinfection. In a preferred embodiment, dispensers can be used that are not equipped with a specific system for data transfer. In this case the detection unit for disinfection treatments in the inventive device contains one or more gas sensors.

Another embodiment can also use dispensers that are equipped with a specific system for data transfer. In this case, the unit for detection of a disinfection treatment in the inventive device can contain preferably at least one additional unit to exchange data with the disinfectant dispenser so that the information about the operation of the disinfectant dispenser can reach the inventive portable device. This data exchange can take place wirelessly.

In another embodiment, dispensers can be used that are equipped with a radio transmitter (preferably an RFID tag) or radio receiver (preferably an RFID reader). In this case, the counterpart (preferably an RFID reader or RFID tag) has to be present in the inventive portable device. A disinfection treatment is then detected by evaluating the proximity to a disinfectant dispenser for a specific minimum period. This method for detecting a disinfection treatment can be combined with additional methods to increase accuracy (e.g., only activating the transmitter or receiver by operating the lever on the disinfectant dispenser).

The inventive portable device is characterized by the fact that any chosen unit for detection of a disinfection treatment is combined with the other inventive elements.

Further embodiments of the hygiene improvement system result from the description the inventive device and the computer system, which is preferably used within a network.

For example, a system can be designed where the data collected by the portable devices can be centrally captured and statistically evaluated. The collected data can be centrally aggregated and evaluated in order to draw conclusions about hygiene improvement.

It is preferably provided that the statistical evaluation of the data collected by the devices can be used as a basis for hygiene improvement measures. This can be achieved by statistically evaluating the data. These statistical evaluations can be performed with regard to the following data:

Staff working hours, particularly as measured by the acceleration sensor

Staff working hours, particularly as measured by the time wherein the inventive portable devices are not placed within the charging station Number of people, particularly number of nurses and doctors Number of people, particularly patients and their case mix Calendar day, time of day Frequency of timely disinfections before indications based on change of location Disinfection frequency after reminders (level 1, 2, 3)

Number of omitted disinfections in spite of reminders

Data on nosocomial infections other clinical data, etc.

The evaluation can be performed using these data types individually or in any combination. These data can be used to verify the success of training measures. Additionally, training measures can be customized for specific insight and problems. Furthermore, the data could be used to identify specific problems within the organizational unit, such as a lack of available disinfectant before dispensers are filled at the beginning of the week, if necessary.

The present invention also intends to provide a method for improving hand hygiene in institutions with strict hygiene requirements, preferably medical facilities, pharmaceutical companies and/or food processing plants, which involves use of a portable device according to the present invention. Especially preferably the method can be implemented in medical facilities.

Specifically, this method can be characterized in that the warning unit activates a signal after a specified number of successive steps, which preferably triggers a switch of a control display to a display of the disinfection state and/or a vibrating alarm. The specified number of successive steps is particularly dependent of the type and organization of the institution for which hygiene should be controlled and/or monitored. In general, the specified number of successive steps can be in the range of 1 to 50—preferably 2 to 20, and ideally 3 to 15 steps. If needed, this number can be customized to the ideal value for a given institution by easy experiments. In hospitals, this number is preferably in the range of 4 to 12—particularly 5 to 10, and ideally 6 to 8 steps.

Preferably, this includes a check whether a disinfection treatment has occurred or was started immediately before or after start of the successive steps. In general, the disinfection state of a user is still adequate even after the previously detailed number of successive steps was exceeded as long as this step sequence has not been interrupted. Correspondingly, a switch of a control display to the disinfection state display and/or a vibrating alarm can be omitted as long as a disinfection treatment was performed or started immediately before or after start of the successive steps.

The expression "successive steps" refers to a movement pattern that is detected by the device in case of an ordinary uniform step sequence. This does not only take acceleration values into account but also especially the time values related to these acceleration values.

In one advantageous embodiment of the method the warning unit can activate a signal (preferably a vibrating alarm) after completing an uninterrupted sequence of uniformly timed steps in which a specified threshold for the number of steps was exceeded.

Here, a consistent, uninterrupted step sequence can be detected if the maximums of the acceleration values in the vertical and horizontal movement that is detected by the step sensor are in a certain timely sequence, ie. maximums always have to succeed each other within a time range of, for example, 0.4 to 1.2 seconds. In an especially preferred embodiment, the time range in which the maximums of the acceleration values have to succeed each other is determined using the portable device wearer's individual movement pattern.

The signal that can be emitted after completing an uninterrupted sequence of uniformly timed steps in which a specified threshold for the number of steps was exceeded, can be triggered individually and exclusively or additionally to the possibly earlier signal that can be triggered when reaching a step threshold (e.g., after 6 steps). Preferably, the signal that can be emitted after completing an uninterrupted sequence of uniformly timed steps in which a specified threshold for the number of steps was exceeded, can be different from the signal that is triggered when reaching a step threshold (e.g., after 6 steps).

In another advantageous embodiment, a further vibrating alarm is emitted after a waiting period—either after reaching the step threshold or after completing the uninterrupted sequence of uniformly timed steps in which a specified threshold for the number of steps was exceeded—if no disinfection treatment was started and/or no further steps were detected within this waiting period. This vibrating alarm should preferably be different from the vibrating alarm that is activated after reaching a step threshold (e.g., after 6 steps).

This enables the device to remind users more forcefully of a necessary hand hygiene action. In an especially beneficial embodiment for many institutions, this waiting period is in the range from 2 to 30 seconds, more preferably 3 to 15 seconds.

Another advantageous embodiment of the method also measures the duration of the disinfection treatment. This can be significant since the prescribed duration of an effective disinfection treatment is normally 30 seconds. The method can therefore only switch the control display to the disinfection state display after the prescribed duration has been reached. For example, a gas sensor, which measures the concentration of the respective gas, can be used to easily determine the duration of the disinfection treatment.

In general, the method detects a number of relatively uniformly timed successive steps. Contrary to conventional step counters, which identify a total number of steps, this invention takes into account a change of location that necessitates hand hygiene—in a specific embodiment, leaving or entering a patient environment. In practice, this change of location is identified by a certain number of uniformly timed successive steps, while single steps during a primarily stationary activity at a certain location or work station are identified by a sequence of inconsistently timed steps. In contrast, changes of location from one work station to another are usually accompanied by a certain minimum number of successive steps that are detected by the device. The device detects the typical distance between two of the device wearer's steps and determines whether each following step occurs within the expected time within the usual range of fluctuation. This needs to be the case for the step to be counted a part of the current uninterrupted step sequence. An uninterrupted step sequence must reach the minimum number of steps (e.g., 6 steps) in order to be evaluated as an indicator for a necessary hand hygiene action. If a step sequence is interrupted after less than the minimum number of steps, this indicates that the current work station (in a specific embodiment the patient environment) has not been exited.

Especially important for the specific embodiment of the method in conjunction with a capture system for hand hygiene actions is the product advantage of the invention wherein mobile detection of hand hygiene is performed. In some cases, the indication for hand hygiene can exist relatively far away from a disinfectant dispenser. If the device wearer then has to walk to the disinfectant dispenser first, there is a much higher likelihood that adequate hand hygiene is neglected, for example, for reasons of convenience or lack of time. Using mobile disinfectant dispensers and detecting their usage with a mobile gas sensor attached to the portable device, this disadvantage can be avoided while still achieving a complete record of hand hygiene behavior.

Using the device in conjunction with a data store and a data transfer unit in institutions with one or more disinfectant dispensers, the data collected by the device(s) can be centrally aggregated and evaluated in order to draw conclusions about improving hygiene. For compliance with privacy regulations and improved user adoption, the portable devices can be distributed anonymously. Specifically, they could be taken from a device pool (such as a charging station) periodically (preferably daily) before starting a shift and returned and charged after the shift ends. This central station could also perform the data transfer to a central computer.

The data collected in such a system can then be used to draw conclusions about improving hygiene. Collected data can include the hand hygiene frequency for each individual (anonymized by using the device pool). The hand hygiene frequency can also be correlated with staff working hours (specifically measured by the acceleration sensor), calendar day, time of day or if necessary other external institutional data (e.g., on the number of nosocomial infections or certain interventions and measures of the institution for increasing the frequency of hand hygiene actions).

The number of indications for hand hygiene and the number of such indications that were actually preceded or followed by a hand hygiene action, or an action after a reminder, can be identified, stored and transferred in order to implement additional targeted measures for increased compliance on the basis of this data.

The inventive device as well as the inventive hygiene improvement system are especially suited for use in medical facilities, such as hospitals and care facilities. In addition, the device and the hygiene improvement system can be used in slaughterhouses, restaurants (e.g., fast food restaurants) and other businesses where food or pharmaceuticals are produced or processed.

Another subject matter of the present invention is the use of a hygiene improvement system for statistical data collection in order to improve and/or maintain hygiene standards.

WORKING EXAMPLES

The following two figures provide examples of a preferred embodiment of the present invention without the invention being limited thereby.

Figure 2:
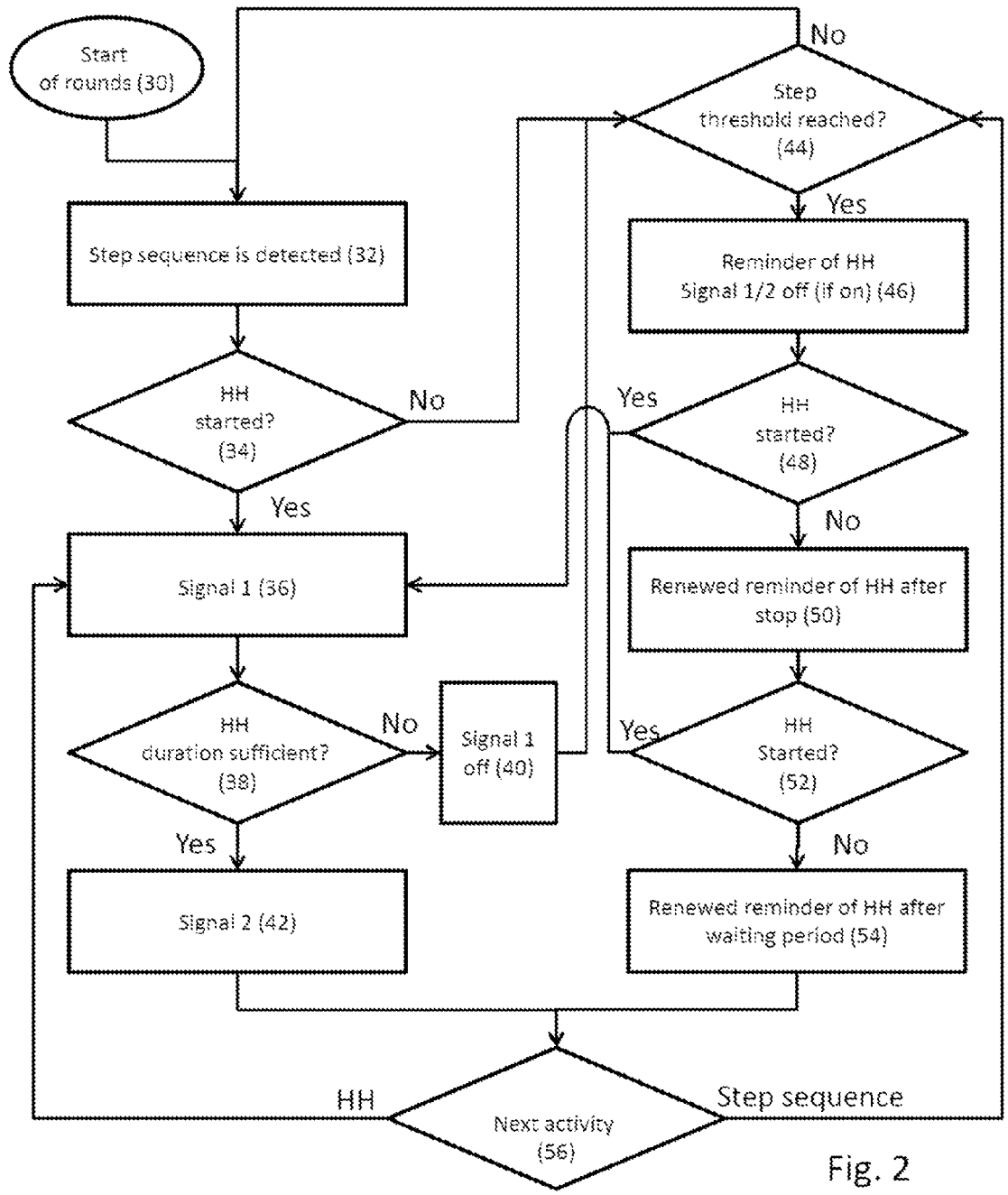

FIG. 1 shows a preferred embodiment of a portable device according to the present invention, and FIG. 2 shows a schematic flow chart.

FIG. 1 describes a preferred embodiment of a portable device according to the present invention (11). A portable device (11) contains one or more warning units (5), a microcontroller operatively connected to a step counter (1), and an acceleration sensor that sends data, which is evaluated with the microcontroller contained in warning unit 5.

In the present embodiment, warning unit 5 is connected to one or more step counters (1) via a data connection in such a way that the data captured with the step counter 1 can be transferred to the warning unit 5, and the transferred data in the warning unit can be processed to activate a signal.

The signaler controlled by the microcontroller can emit, for example, visual or acoustic signals or vibrations. Correspondingly, a portable device (11) can in some cases contain an additional LED (6) and/or an alarm (7) with especially preferred embodiments including both an LED (6) and an additional alarm (7). The present device can also be equipped with an additional I/O element (8), for example, a touchscreen.

Aside from a warning unit (5) and a step counter (1) an inventive device also contains at least one detection unit for disinfection treatments (2), which is designed as a gas sensor in the embodiment described by FIG. 1. In the present embodiment, the data from the gas sensor can be evaluated by the warning unit 5.

Preferably, a portable device (11) can contain one or more infrared sensors (3) that can detect special areas so that the signal in specific locations can be customized according to needs. The portable device can also include another input element (4) that enables the wearer to configure settings. The infrared sensor (3) and the input element (4) are connected to the warning unit (5).

Additionally, the portable device (11) can contain one or more data stores (9) and one or more data communication interfaces (10). In the embodiment shown in FIG. 1, the data store (9) is connected to the warning unit. This design enables a statistical evaluation of the performed disinfection treatment.

In the present embodiment, evaluation of signals from the elements 1-4 according to suitable algorithms, output of signals in elements 6-8, storage of events in element 9, and output on element 10 takes place in warning unit 5 by means of a suitable data processing unit, specifically in form of a microcontroller, which allows for easy portability of device 11.

Device 11 should preferably be worn at waist height on the user's work clothes to ensure optimal detection of disinfectant by gas sensor 2. When performing hand hygiene actions, the disinfectant is repeatedly rubbed into the user's hands for the time of exposure. This normally includes moving your hands with typically bent arms at waist height close to the body. This produces a very high gas concentration of the disinfectant, which enables a positive differentiation between the gas cloud from the device wearer's hand hygiene action and hand hygiene actions in the surroundings, e.g., by other people, especially by measuring the gas concentration repeatedly, provided the concentration threshold for the detection of a hand hygiene action was appropriately parameterized.

The portable device (11) can be connected to a computer system (12) via a data transfer unit (10). The computer system (12) can be part of a network (13), in which data connections can be created via common standards, such as wired LANs, or wireless technologies, like WLAN.

FIG. 2 demonstrates the interaction between step sequences and necessary disinfection actions, for example, when doing rounds in a hospital, as well as the corresponding inventive method.

Ward rounds consist of a sequence of typically uninterrupted steps to the next patient and patient treatments with typically interrupted step sequences.

At the start of the round (30) a step sequence is detected in process step (32) of in the inventive method determining the number of uniformly timed successive steps.

In decision step (34) it is verified whether hand hygiene (HH) was started. This check is preferably done by a gas sensor.

If the sensor identifies a hand hygiene (HH) start, a signal 1 is emitted according to process step (36) (in a preferred embodiment, for example, a green blinking light). In decision step (38), the device checks for a sufficient disinfection action.

If decision step (38) concludes that the minimum duration was not sufficient, signal 1 is deactivated in process step (40) and decision step (44) checks whether the step threshold was reached.

If in another preferred embodiment the gas sensor in decision step (38) measures a minimum gas concentration during a minimum time, which indicates a hand hygiene action, signal 2 is emitted in process step (42) (in a preferred embodiment a continuous green light), regardless of the potential continuation of the step sequence and beyond its completion.

Signal 2 continues to be emitted during the current step sequence and after its completion to indicate that a sufficient hand hygiene action was performed. After completion of the step sequence, indicated by the absence of a following step within the expected time, decision step (56) waits for further activity, in particular whether a new step sequence or a renewed hand hygiene action is started. A renewed hand hygiene action leads to a flow according to process step (36), whereas a newly started step sequence results in a check according to decision step (44).

If it is determined in decision step (34) that no hand hygiene action was started, decision step (44) measures and checks whether a predefined step threshold has been reached—in a preferred embodiment, for example, 6 consistent successive steps.

If the step threshold was not reached in decision step (44), the device continues to monitor the current step sequence, as illustrated in process step (32). Simultaneously with and/or at the end of the current step sequence before reaching the step threshold, the device checks whether a hand hygiene action was started (decision step (34)). If yes, process step (36) applies, if no, the device continues to check in decision step (44) whether an uninterrupted step sequence reaches the step threshold.

If the device determines in decision step (44) that the step threshold has been reached, potentially activated signals 1 and 2 are turned off in process step (46), and the signaler emits a hand hygiene reminder to the device wearer—in a preferred embodiment by means of a vibrating alarm. If the device then detects the start of a hand hygiene action in decision step (48), process step (36) applies for the following method. If not, another reminder is sent in process step (50)—in a preferred embodiment by means of a vibrating alarm—after completion of the current step sequence. If the device then detects the start of a hand hygiene action in decision step (52), process step (36) applies for the following method. If not, the device sends another, preferably longer, reminder signal in process step (54) after a waiting period (in a preferred embodiment, for example, after 4-5 seconds).

Afterwards, decision step (56) waits for further activity, specifically either a new step sequence or a new hand hygiene action.

Altogether this results in a closed circuit of decision and process steps.

The following practical example of the method illustrates the typical flow of a round in a hospital without limiting the invention in any way. After a building-specific analysis, a default value of, for example, 6 steps is set as the threshold for an indication for hand hygiene in the evaluation unit of the device.

The device wearer (e.g., doctor or nursing staff) enters a room. According to typical hospital rules, this requires a hand hygiene action. When entering a room the device will typically detect more than 6 steps. Correspondingly, the device signals an indication for hand hygiene (e.g., by turning off a green LED that is turned on after a hand hygiene action or by means of a vibrating alarm to the device wearer).

If a successful hand hygiene action is performed, the gas sensor detects a chemical substance for a specific time span and then turns on a signal (for example, a green LED).

Possible steps that are taken during the hand hygiene action do not lead to a new hand hygiene indication and are treated correspondingly by the device.

During the duration of the hand hygiene action the device wearer reaches the patient. The status LED lights up green to indicate a successful hand hygiene action. Within the patient environment, the device wearer normally does not take multiple consistent steps but single, interrupted steps. These single steps are not identified as a step sequence with at least 6 steps. Therefore, the hand hygiene status displayed on the device rightly does not change: Objectively, there is no new indication for hand hygiene due to a change of location.

In another particularly advantageous embodiment, an uninterrupted walk with a consistent step sequence that was already started during a hand hygiene action does not lead to a new hand hygiene indication since normally the hands are still hygienic when reaching the destination (opening a door on the way would result in a detectable deviation from the consistency of the step sequence). This enables the user to perform activities at the destination while the LED rightly indicates a sufficient hygiene status.

If the device wearer moves for more than 6 steps within a continuous, uninterrupted step sequence, this would, in practice, almost always result in a hand hygiene indication. Examples for this include walking to a cupboard in the patient's room, walking to the desk for a note, or walking to the window. In this case the indications for hand hygiene according to WHO rules, typical hospital rules and detection of a step sequence with more than 6 steps are the same.

After contact with the patient and leaving a patient environment, another change of location with typically more than 6 steps takes place. Here too, the indications for hand hygiene according to WHO rules and typical hospital rules as well as the detection of a step sequence with more than 6 steps are the same.

A specific embodiment of the method can also send a reminder to the wearer immediately after completing 6 uninterrupted steps during a walk, and another reminder after completing the uninterrupted walk (for example, after 20 steps, as soon as the device wearer reaches the destination, such as the next patient's bed), and a renewed reminder of the necessary hand hygiene action a few seconds after completing the uninterrupted walk if no start of a hand hygiene action was detected by the gas sensor in the meantime. This way, the device can remind the user exclusively of actually necessary hand hygiene actions but in these cases send forceful and if needed repeated reminders.

The invention claimed is:

1. Method for improving hygiene in facilities having high hygienic standards, including use of a portable device comprising at least one warning unit that cooperates with a unit for detection of a disinfection treatment in such a way that a signal can be activated, wherein said warning unit is operatively connected to at least one step counting unit, in which the warning unit triggers a signal after completing an uninterrupted sequence of uniformly timed steps in which a specified threshold for the number of steps was exceeded.

2. Method according to claim 1, wherein the step counting unit comprises an acceleration sensor enabling the identification of a movement pattern using software corresponding to a specified number of successive steps and/or a number of steps with a relatively uniform time between them.

3. Method according to claim 1, wherein the detection unit for disinfection treatments includes at least one gas sensor.

4. Method according to claim 3, wherein the gas sensor detects alcohol.

5. Method according to claim 4, wherein the gas sensor detects ethanol and/or propanol.

6. Method according to claim 1, wherein the warning unit includes a control display for indicating a disinfection state.

7. Method according to claim 1, wherein the warning unit includes a unit for generating a vibrating alarm.

8. Method according to claim 1, wherein the portable device contains one or more IR sensors operatively connected to the warning unit.

9. Method according to claim 1, wherein the portable device includes one or more data stores that can store time data, hand hygiene actions, and/or detected hand hygiene indications.

10. Method according to claim 9, wherein the one or more data stores is or are connected to the warning unit and/or the detection unit for disinfection treatments.

11. Method according to claim 1, in which the warning unit activates a signal after a specified number of successive steps.

12. Method according to claim 11, in which the duration of the disinfection treatment is measured.

13. Method according to claim 11, in which the signal triggers a switch of a control display to a display of the disinfection state and/or a vibrating alarm.

14. Method for improving hygiene according to claim 1, wherein the facilities having high hygienic standards are selected from the group consisting of medical facilities, pharmaceutical companies, food processing plants.

15. Method according to claim 1, in which the signal is a first vibrating alarm.

16. Method according to claim 15, in which a second vibrating alarm is emitted after a waiting period if no disinfection treatment is performed and/or no further steps are detected within that waiting period.

* * * * *